United States Patent [19]

van der Jagt

[11] Patent Number: Plant 5,974

[45] Date of Patent: May 5, 1987

[54] CHRYSANTHEMUM NAMED 'WHITE REDEMINE'

[75] Inventor: Martinus van der Jagt, Ter Aar, Netherlands

[73] Assignee: Chrysanthemum Breeders Association N.V., Willemstad, Netherlands Antilles

[21] Appl. No.: 767,661

[22] Filed: Aug. 21, 1985

Related U.S. Application Data

[63] Continuation of Ser. No. 599,326, Apr. 12, 1984, abandoned.

[51] Int. Cl.[4] ..... A01H 5/00

[52] U.S. Cl. ..... Plt./78

[58] Field of Search ..... Plt./78

*Primary Examiner*—James R. Feyrer

*Attorney, Agent, or Firm*—Parkhurst & Oliff

[57] ABSTRACT

A new and distinct cultivar of Chrysanthemum plant named 'White Redemine' bearing large sized broken-white blooms with a green-white center having a performance of seventeen days.

3 Drawing Figures

This is a continuation of application Ser. No. 599,326, filed Apr. 12, 1984, now abandoned.

BACKGROUND OF THE NEW PLANT

The new plant of the present invention relates to the Chrysanthemum genus.

ORIGIN AND HISTORY OF THE NEW PLANT

The new plant according to the present invention comprises a new and distinct cultivar of Chrysanthemum plant which is a mutant of Chrysanthemum named 'Redemine'. The parent being dawn pink and the mutant being white in color. The new cultivar was discovered by Martinus van der Jagt in October, 1983 at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and broken-white color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage and petiole of the new cultivar.

DESCRIPTION OF THE NEW PLANT

This new variety of chrysanthemum is of the botanical classification *Chrysanthemum morifolium,* named 'White Redemine'. When grown in the vicinity of Ter Aar, Holland, it has a response time of approximately ten weeks. This new variety produces medium sized broken-white blooms with a green-white (with some red) center having a two and one-half weeks performance. This new variety Chrysanthemum has been found to retain its distinctive characteristics throughout successive propagations and may be planted year round under conventional greenhouse conditions in Holland.

The following is a description of the plant and characteristics that distinguish it over related known varieties and its antecedents:

Botanical classification: *Chrysanthemum morifolium.*

Bud:
- *Size.*—Medium.
- *Form.*—Round and high.
- *Color.*—Uranium green (RHS 663/3) to white.

Bloom:
- *Size.*—Medium.
- *Fully expanded.*—6–7 cm.
- *Borne.*—Single, sometimes several.
- *Stems.*—Strong.
- *Forms.*—Compact spider form.
- *Permanence.*—Good, 18 days.

Color:
- *Center of flower (Disc Floret).*—Most to Chartreuse Green (RHS 663/2) with a spot of some red (RHS 022/2).
- *Base of petals.*—Chartreuse Green (RHS 663/3).
- *Inside of petals.*—Chartreuse Green (RHS 663/3).
- *Reverse of petals.*—Chartreuse Green (RHS 663/3).
- *Outer petals.*—Chartreuse Green to White.
- *Tonality from a distance.*—A broken white spider with a green tone. A scant blush of red may be exhibited as a central spot.
- *Discoloration.*—Yes, to white.

Petals:
- *Texture.*—Spider small tubular petals in the center, bigger ones on the edge of the flower.
- *Number.*—In excess of 150.
- *Arrangement.*—Imbricated (decorative).
- *Persistence.*—Strong, do not reflex at all.
- *Fragrance.*—Normal.

Reproductive organs:
- *Stamen.*—Few and small.
- *Pollen.*—Few (in the petals).
- *Styles.*—Columnar and very small.
- *Length.*—Normal.
- *Stigmas.*—Normal, very small and mostly green.
- *Ovaries.*—Enclosed in calyx.

Plant:
- *Form.*—Herbaceous.

*Growth.*—Vigorous.

*Height.*—110 cm. (approx.).

*Length of peduncle.*—Near the top — 6–7 cm. (approx.). Near the middle — 15 cm. (approx.). Near the bottom — 20–21 cm. (approx.).

*Internodes.*—3.5–4 cm.

*Response time.*—10.5 to 11 weeks.

Foliage:

*Color.*—Normal.

*Size.*—Length 13 cm. and width 8 cm.

*Quantity.*—Normal.

*Shape.*—Pointed oval.

*Texture.*—Normal.

*Ribs and veins.*—Light and sharp.

*Margin.*—Deeply undulated.

*Leaf underside.*—Smooth to heavy.

In the description above, color references are made to the "Horticultural Colour Chart I & II" issued by the British Colour Council in collaboration with The Royal Horticultural Society, Copyright Robert F. Wilson, Vol I, 1938; Vol II, 1941, printed by Henry Stone & Son, Ltd., Banbury, England.

What is claimed is:

1. A new and distinct cultivar of Chrysanthemum named 'White Redemine', as described and illustrated in the foregoing specification and accompanying drawings.

* * * * *

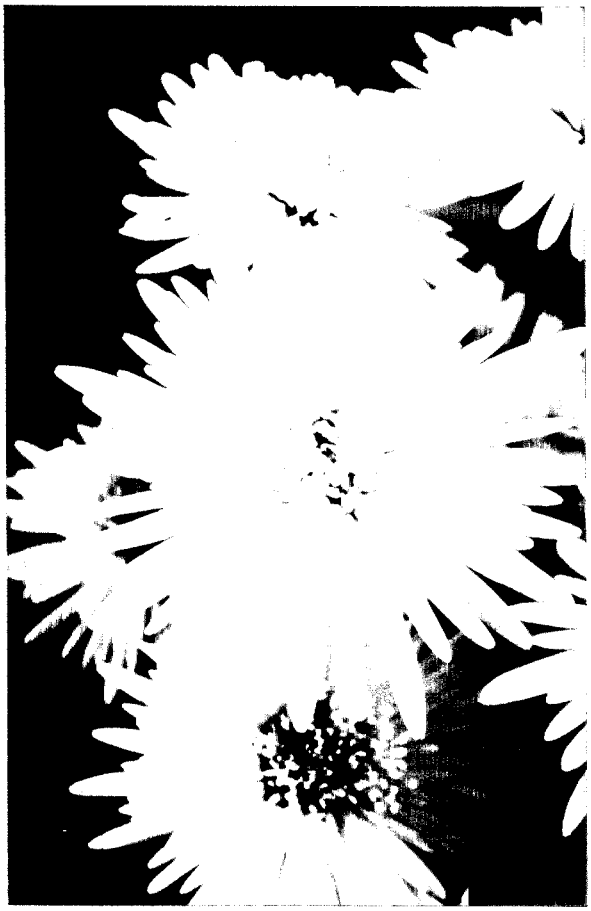

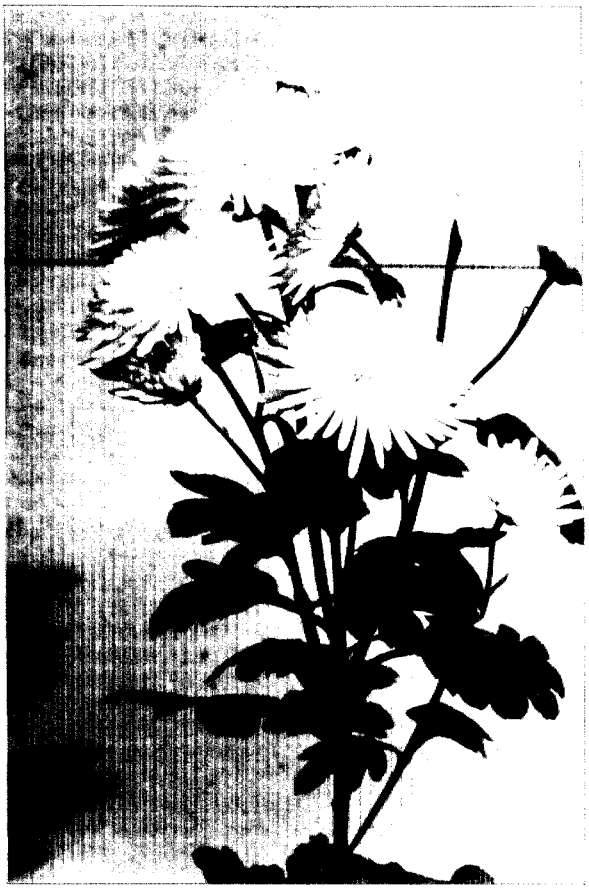

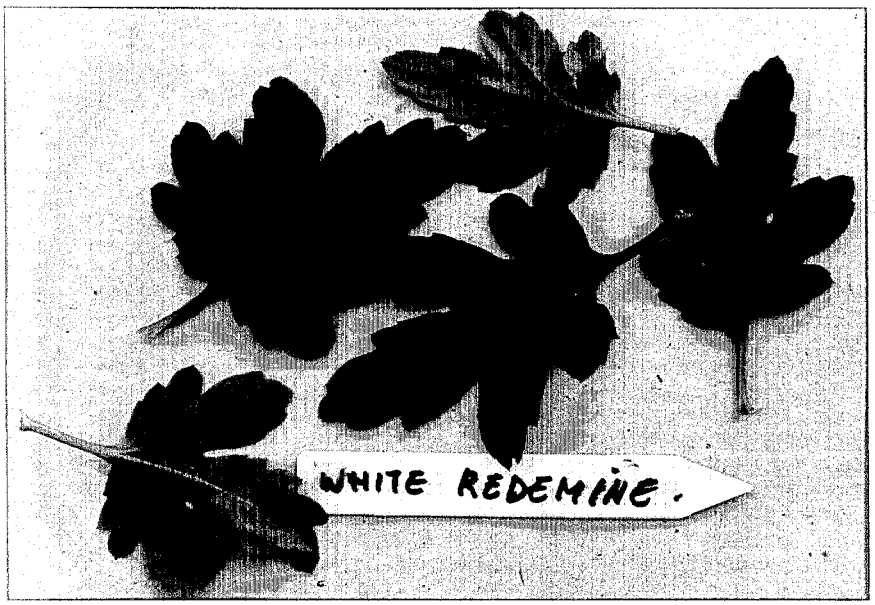
WHITE REDEMINE.